(12) United States Patent
Yeh et al.

(10) Patent No.: US 8,709,720 B2
(45) Date of Patent: Apr. 29, 2014

(54) METHODS AND KITS FOR PREDICTING THE RESPONSIVENESS OF HEPATOCELLULAR CARCINOMA PATIENTS TO 5-FLUOROURACIL-BASED COMBINATION CHEMOTHERAPY

(76) Inventors: Chau-Ting Yeh, Gueishan Township, Taoyuan County (TW); Kung-Hao Liang, Gueishan Township, Taoyuan County (TW)

( * ) Notice: Subject to any disclaimer, the term of this patent is extended or adjusted under 35 U.S.C. 154(b) by 0 days.

(21) Appl. No.: 13/411,306

(22) Filed: Mar. 2, 2012

(65) Prior Publication Data
US 2013/0230847 A1 Sep. 5, 2013

(51) Int. Cl.
*C12P 19/34* (2006.01)
*C12Q 1/68* (2006.01)
*A61K 48/00* (2006.01)
*C07H 21/04* (2006.01)

(52) U.S. Cl.
USPC ........... 435/6.1; 435/91.1; 424/9.1; 536/23.1; 536/24.3

(58) Field of Classification Search
None
See application file for complete search history.

(56) References Cited

PUBLICATIONS

Jayapal (Clinical and Experimental Pharmacology and Physiology, 2006, vol. 33, pp. 496-503).*
Shi (Clin Chem, 2001, 47:2, 164-172).*
Buck et al (Biotechniques (1999) 27(3):528-536).*
refSNP Cluster report: rs9679162 (available at www.ncbi.nlm.nih.gov/projects/SNP/, printed May 2013, pp. 1-5).*
Chiang et al. (Cancer Res, 2008 68:6779-6788).*
Liang (Pharmacogenomic, 2011, 12(7): 1061-1073).*

* cited by examiner

*Primary Examiner* — Sarae Bausch
(74) *Attorney, Agent, or Firm* — Muncy, Geissler, Olds & Lowe, P.C.

(57) ABSTRACT

Disclosed herein is a method for identifying single nucleotide polymorphisms of a target nucleic acid for predicting whether a patient suffering from hepatocellular carcinoma will respond to a 5-fluorouracil (5-FU)-based combination chemotherapy. In some embodiments, biological sample derived from the patient is processed to determine the presence of a T/T genotype of rs9679162 GALNT14 gene. The presence of the above-identified genotype is an indication that the patient is responsive to the 5-FU-based combination chemotherapy.

6 Claims, 3 Drawing Sheets

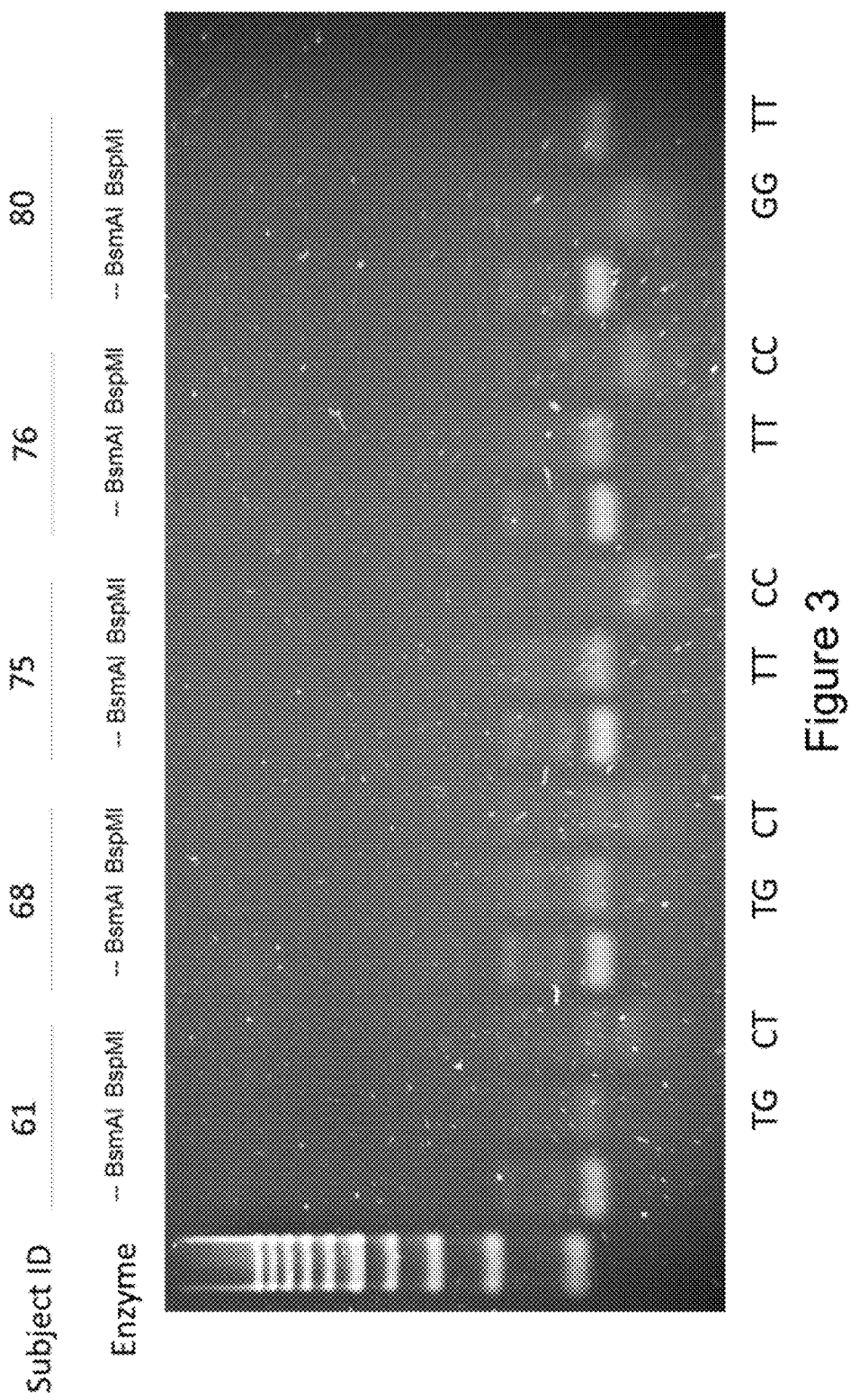

tions or extra hepatic metastasis. However, for patients who had developed extra hepatic metastasis or had poor liver functions, systemic chemotherapy remains an option.

METHODS AND KITS FOR PREDICTING THE RESPONSIVENESS OF HEPATOCELLULAR CARCINOMA PATIENTS TO 5-FLUOROURACIL-BASED COMBINATION CHEMOTHERAPY

BACKGROUND OF THE INVENTION

1. Field of the Invention

The present disclosure relates to pharmacogenomics. More particularly, the disclosure relates to selecting a suitable chemotherapy for a patient suffering from hepatocellular carcinoma (HCC) based on the patient's GALNT14 genotypes.

2. Description of Related Art

Worldwide, HCC ranks as the fifth most common solid malignant tumor and the third leading cause of cancer death. If diagnosed in its early stage, HCC can be treated by surgical resection or nonsurgical ablation procedures; albeit a high recurrent rate of approximately 70% remains. Liver transplantation, which results in the complete removal of tumor cells and replacement of cirrhotic liver tissues, is the best therapeutic modality for eligible patients. Yet, for patients with unresectable HCC, standard therapy has not been established. Transcatheter arterial chemoembolization is an effective palliative treatment that prolongs survival time in HCC patients without main portal vein occlusion or extra hepatic metastasis. However, for patients who had developed extra hepatic metastasis or had poor liver functions, systemic chemotherapy remains an option.

Chemotherapies using a single agent are not effective in treating advanced HCC. Prior research demonstrated that, among various tested single agents, only doxorubicin achieved a response rate of 32%. Thus, in some clinical trials, several combination formulae have been devised to investigate their efficacies in treating advanced HCC. Among these regimens, only three combination formulae achieved a higher response rate. These three regimens include, combination of epirubicin and etoposide (response rate: 39%); combination of cisplatin, doxorubicin, 5-flurouracil (5-FU), and α-interferon (response rate: 26%); and combination of 5-FU, mitoxantrone, and cisplatin (FMP, response rate: 27%). Despite having a substantial response rate, profound side effects occurred in almost all systemic chemotherapeutic agents, hindering their clinical uses in far advanced HCC. Moreover, the prognosis of these combination formulae is poor; for example, the survival time of the FMP treatment is less than 1 year. Furthermore, these treatments manifest a high degree of variability in the responses of individual patients. Hence, patients and doctors are confronted with a tough situation when choosing a treatment.

In view of the foregoing, there exists a need in the art a means for selecting a suitable combinational chemotherapy for a HCC patient so that suitable therapeutic regimen may be administered to the patient.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on, at least in part, the discovery that polymorphisms within the UDP-N-acetyl-alpha-D-galactosamine:polypeptide N-acetylgalactosaminyltransferase 14 (GalNAc-T14, or GALNT14) gene are associated with the responsiveness of hepatocellular carcinoma in patients to a 5-FU-based combination chemotherapy. Therefore, the genotype of single nucleotide polymorphism (SNP) located at specific position of the GALNT14 gene is predictive of the responsiveness of HCC patients to a 5-FU-based combination chemotherapy, and this discovery has tremendous therapeutic potential.

In one aspect; the present disclosure is directed to a method for selecting HCC patients that are suitable for treatment with 5-FU-based combination chemotherapy based on the patient's GALNT14 genotype(s).

According to one embodiment of the present disclosure, the method comprises determining the presence of a T/T genotype of rs9679162 of the HCC patient. Results provided in the Examples of this application indicate that the presence of the T/T genotype in HCC patients is positively related to the therapeutic effect of the 5-FU-based combination chemotherapy administered thereto, and therefore, the presence of the T/T genotype is indicative that the HCC patient will respond to the 5-FU-based combination chemotherapy.

In one embodiment of the present disclosure, the 5-FU-based combination chemotherapy consists of 5-FU, mitoxantrone, and cisplatin.

Optionally, the hepatocellular carcinoma is advanced hepatocellular carcinoma.

The genotype is determined by amplifying a target nucleic acid comprising the afore-mentioned polymorphic site by using a first forward primer having the sequence of TCACGAGGCCAACATTCTAG (SEQ ID No: 1) and a first reverse primer having the sequence of TTAGATTCTGCATGGCTCAC (SEQ ID No: 2). In a further embodiment, the target nucleic acid is further amplified by using a second forward primer having the sequence of GAAAGCAAAGAGATATATATAACGTCT (SEQ ID No: 3) and a second reverse primer having the sequence of ACCACCTTCCCCTTATTCACCTG (SEQ ID No: 4). The second forward primer is designed to introduce a restriction enzyme cutting site which encompasses the polymorphic site. Therefore, in an optional embodiment, the rs9679162 GALNT14 genotype is determined by a restriction enzyme that recognizes the nucleotide sequence of GTCTC. The restriction enzyme may be BsmAI, BsmBI (Esp3I), or isoschizomers thereof. Alternatively or additionally, the rs6752303 GALNT14 genotype is determined by a restriction enzyme that recognizes the nucleotide sequence of ACCTGC. The restriction enzyme may be BspMI or isoschizomers thereof.

In optional embodiments, the method further comprises determining the presence of at least one genotype selecting from the group consisting of, A/A and A/T genotype of rs12999804, C/C genotype of rs10209881, C/C genotype of rs6752303, C/C genotype of rs5009910, G/G and G/T genotype of rs12613732, and C/C genotype of rs7608731.

In another aspect, the present invention is related to a kit for predicting the responsiveness of a HCC patient to a 5-FU-based combination chemotherapy.

According to one embodiment of the present disclosure, the kit comprises a pair of primers suitable for amplifying a target nucleic acid comprising a SNP of GALNT14 gene in a HCC patient, wherein the SNP comprises rs9679162. In particular, the kit includes a first pair of primers comprising a first forward primer having the sequence of TCACGAGGCCAACATTCTAG (SEQ ID No: 1) and a first reverse primer having the sequence of TTAGATTCTGCATGGCTCAC (SEQ ID No: 2).

In an optional embodiment, the kit further includes a second pair of primers comprising a second forward primer having the sequence of GAAAGCAAAGAGATATATA ACGTCT (SEQ ID No: 3) and a second reverse primer having the sequence of ACCACCTTCCCCTTATTCACCTG (SEQ ID No: 4) so as to give an amplicon after the amplification.

Optionally, the kit may further comprise a restriction endonuclease specific to one of the GALNT14 genotypes. For example, a restriction enzyme such as BsmAI or isoschizomers thereof that recognizes the nucleotide sequence of GTCTC in the amplicon may be used to determine the genotype of rs9679162 of GALNT14 gene.

Alternatively, the kit comprises at least one nucleotide probe specific for forming a hybridization complex with the target nucleic acid of the HCC patient. In practice, the probe may have a detectable label attached thereto. Examples of the detectable label include, but are not limited to, radioactive labels, fluorescent labels, chemiluminescent labels, bioluminescent labels, and enzyme labels.

In optional embodiments, the kit further comprises additional primers suitable for amplifying a target nucleic acid encompassing at least one SNP selected from the group consisting of, rs12999804, rs10209881, rs6752303, rs5009910, rs12613732, and rs7608731.

In yet another aspect, the present disclosure is directed to a nucleic acid chip for screening for the GALNT14 gene polymorphism.

According to one embodiment of the present disclosure, the nucleic acid chip comprises a solid support and a first nucleic acid probe immobilized on the solid support. The first nucleic acid probe is specific for detecting the T/T genotype of rs9679162.

Optionally, the nucleic acid chip comprises one or more additional nucleic acid probe, each of which is specific for detecting one of the following genotypes: A/A and A/T genotype of rs1299804, C/C genotype of rs10209881, C/C genotype of rs6752303, C/C genotype of rs5009910, G/G and G/T genotype of rs12613732, and C/C genotype of rs7608731.

Still optionally, the nucleic acid probe has a detectable label attached thereto. Examples of the detectable label include, but are not limited to, radioactive labels, fluorescent labels, chemiluminescent labels, bioluminescent labels, and enzyme labels.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 3 is a photograph depicting the electrophoresis result according to one example of the present disclosure.

DESCRIPTION

Figure 1:
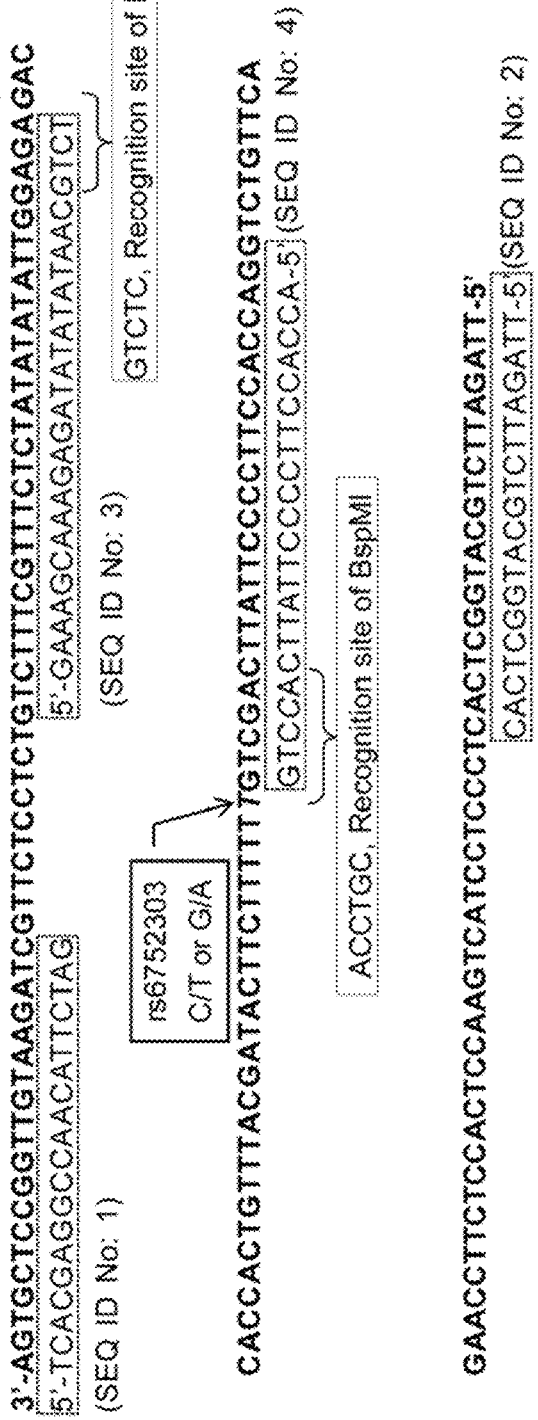
FIG. 1 is a schematic diagram illustrating a target nucleic acid (SEQ ID No: 5) containing rs9679162, and a first and second pair of primers for amplifying the target nucleic acid, according to one example of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "hepatocellular carcinoma" (or "HCC" for short) refers to a malignant tumor of hepatocellular origin. HCC is a type of liver cancer. HCC may undergo hemorrhage and necrosis because of a lack of fibrous stroma. "Advanced hepatocellular carcinoma," refers to HCC that is not amenable to cure by local modalities of treatment, such as surgery or radiotherapy. Advanced HCC may refer to a locally advanced HCC or it may refer to metastatic HCC. The term "metastatic hepatocellular carcinoma" refers to HCC that has spread from liver to another part of the body. Advanced HCC may also be unresectable, that is, it has spread to surrounding tissue and cannot be surgically removed.

In general, a "5-FU-based combination chemotherapy" includes 5-FU and at least one other chemotherapy agent, which includes but is not limited to, cisplatin, mitoxantrone, doxorubicin, fluoropirimidines, mitomycin C, and interferon-alpha. According to one example of the present disclosure, the -FU-based combination chemotherapy comprises 5-FU, cisplatin, and mitoxantrone.

The term "nucleotide" refers to a chemical compound that consists of a heterocyclic base, a sugar, and one or more phosphate groups. In the most common nucleotides the base is a derivative of purine or pyrimidine, and the sugar is the pentose deoxyribose or ribose. The purines include adenine (A), and guanine (G); the pyrimidines include cytosine (C), thymine (T), and uracil (U). The term "nucleotide sequence"

is used to refer to the ordering of nucleotides in an oligonucleotide or polynucleotide in a single-stranded form of nucleic acid. The term "nucleic acid" as used herein designates single- or double-stranded RNA, mRNA, and DNA including cDNA and genomic DNA. Unless specified otherwise, the left-hand end of single-stranded nucleotide sequences is the 5' end; and the right-hand end of single-stranded nucleotide sequences is the 3' end. The term "downstream" refers to a nucleotide sequence that is located 3' to a previously mentioned nucleotide sequence. The term "upstream" refers to a nucleotide sequence that is located 5' to a previously mentioned nucleotide sequence.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. In the context of the present disclosure, a "single nucleotide polymorphism" (SNP) refers to a variation occurring when a single nucleotide in the genome (or other shared sequence) differs between members of a species. The SNPs listed in the present disclosure are referenced with a SNP identifier assigned by dbSNP of National Center for Biotechnology Information (US), and the variant nucleotides at the polymorphic position are indicated as the SNP on the antisense (non-coding) strand. Since the nucleotide sequences of the sense and antisense strands are complementary to each other, the identification of the polymorphic base on one strand would reveal the polymorphic base on the other strand. For example, T/G means T and G are the polymorphic bases on one strand (e.g., antisense strand), and these polymorphic bases are equivalent to A/C on the other strand (e.g., sense strand).

As used herein, the term "primer" refers to a single-stranded polynucleotide capable of acting as a point of initiation of template-directed DNA synthesis under appropriate conditions (e.g., buffer, salt, temperature, and pH) in the presence of nucleotides and an agent for nucleic acid polymerization (e.g., a DNA-dependent or RNA-dependent polymerase). In the present disclosure, the sequence aimed to be amplified is referred to as the "target nucleic acid." For the amplification of double-stranded DNA, a primer pair (i.e., a forward primer and a reverse primer) is often employed so as to enable the amplification of both the coding and non-coding strands. According to common practice, the "forward primer" has a sequence substantially the same as a sequence of the upstream of the target nucleic acid of the coding strand such that the forward primer may hybridize (or anneal) with the non-coding strand. On the other hand, the "reverse primer" has a sequence substantially complementary to a sequence of the downstream of the target nucleic acid of the coding strand so that the reverse primer may hybridize (or anneal) with the coding strand.

As used herein, the term "probe" refers to a nucleic acid capable of binding to a target nucleic acid of complementary sequence through one or more types of chemical bonds, usually through complementary base pairing, usually through hydrogen bond formation, thus forming a duplex structure.

The term "probe" according to the present disclosure refers to a single-stranded synthetic oligonucleotide which is designed to specifically hybridize with the target oligonucleotide to form a duplex structure.

The term "hybridization", as used herein, refers to the formation of complexes between nucleotide sequences which are sufficiently complementary to form complexes (or hybrids) via Watson-Crick base pairing or non-canonical base pairing. The hybridization may take place between two DNA strands, two RNA strands, or one DNA and one RNA strand. The hybridization occurs under a variety appropriate conditions (e.g. temperature, pH, salt concentration, etc.) that are well known in the art of molecular biology. It would be appreciated by any skilled artisan that the hybridizing sequences need not have perfect complementarity.

The term "prediction," in connection with the method/kit according to the invention for determining the responsiveness of hepatocellular carcinoma to a 5-fluorouracil (5-FU)-based combination therapy, refers to the ability to foretell or infer whether a subject will respond in a positive manner, (e.g., whether a patient will be responsive) or a negative manner to the therapy. In one embodiment, the prediction relates to the extent of those responses. In another embodiment, the prediction relates to whether and/or the probability that a patient will survive or improve following treatment, and for a certain period of time without disease recurrence. For example, the predictive methods of the present disclosure may be used clinically to make treatment decisions by choosing the most appropriate treatment modalities for any particular patient. The predictive methods of the present disclosure are valuable tools in predicting whether a patient is likely to respond favorably to a treatment regimen, including for example, administration of a 5-FU-based combination therapy, or whether long-term survival of the patient, following a therapeutic regimen is likely.

In the context of the present disclosure, the term "responsiveness" refers to a measurable response, including complete response (CR), partial response (PR), stable disease (SD) and progressive disease (PD). In particular, the responsiveness of the HCC to the therapy is evaluated according to the response evaluation criteria in solid tumors proposed by Eisenhauer EA et al. (*European J. Cancer* 45, 228-247 (2009)). By "complete response" is intended the complete disappearance of all target lesions without any residual lesion. It shall be noted that the complete response does not always mean the disease has been cured. "Partial response" refers to a decrease of at >30% decrease in tumor mass without progression in any target lesion or appearance of a new lesion. "Stable disease" is defined as either a <30% decrease or a <20% increase of total tumor mass. By "progressive disease" is meant a >20% increase in total tumor mass or appearance of a new lesion. Disease control is achieved in patients without progressive disease, and hence, patients with CR, PR, and SD are evaluated as "responders." By contrast, patients who present a progressive disease are termed "non-responders."

As used herein, the term "survival", refers to the act or fact of living. The term "disease-free survival" is intended to refer to the lack of tumor recurrence and/or spread. The phrase "overall survival" refers to the fate of the patient after diagnosis, regardless of whether the patient has a recurrence of the tumor.

Diversity of chemotherapeutic responses has long been recognized, largely owing to the underlying heterogeneities in cancer biology, variations in physiological function and distinctions in patients' genetic profiles. Therefore, one objective of the present disclosure aims at providing molecular markers associated with the objective response to 5-FU-based combination chemotherapy. Once identified, these molecular markers are useful in predicting the responsiveness of hepatocellular carcinoma in a patient to a 5-FU-based combination chemotherapy, and medical practitioners may design treatment regimens tailored for individuals based on the prediction.

In an exploratory phase, we screened genomes of patients who had been through the first course of 5-FU-based combination chemotherapy. A total of 153 SNPs has significance levels (allelic $X^2$ test p-values) smaller than 0.001. Among them, 16 SNPs on chromosomes 2, 6, and 15, with X achieving p-values smaller than 0.0001 (data not shown). For further validation, the SNP, rs9679162, is selected. The results suggest that rs9679162 is highly associated with the responsiveness of the HCC patients to 5-FU-based combination chemotherapy. Therefore, the present invention is at least based on the discovery that one or more SNP of GALNT14 genes is suitable for use as a molecular marker, which is predictive of the responsiveness of HCC patients to a 5-FU-based combination chemotherapy.

In view of the foregoing, one aspect of the present disclosure is directed to a kit for identifying single nucleotide polymorphisms of a target nucleic acid for predicting whether a patient suffering from hepatocellular carcinoma will respond to a 5-FU-based combination chemotherapy.

The kit is useful for identifying the presence or absence of one or more SNPs in a target nucleic acid of a HCC patient. Generally, the target nucleic acid may be derived from clinical samples collected from HCC patients. The kit may comprise materials for amplifying the target sequence that encompasses at least one polymorphic sites of GALNT14 gene, and means for identifying the genotype at the polymorphic sites.

According to one embodiment of the present disclosure, the kit comprises a first pair of primers for amplifying a target nucleic acid comprising rs9679162 of GALNT14 gene. Any suitable primers may be employed herein for amplifying the target nucleic acid containing rs9679162. Persons skilled in the art are familiar with various well-known methods in designing primers for use in conventional PCR or variants thereof.

In optional embodiments, the kit comprises primers for amplifying the afore-amplified target nucleic acid for the presence or absence of at least one additional SNP selected from the group consisting of: rs12999804, rs10209881, rs6752303, rs5009910, rs12613732, and rs7608731. In some embodiments, the target nucleic acid may encompass one polymorphic site; while in other embodiments, the target nucleic acid may encompass two or more polymorphic sites.

As an example, but not a limitation, a first forward primer and a first reverse primer are used in the kit for the amplification of the target nucleic acid. FIG. 1 is provided as an example to facilitate the understanding of the present disclosure. Illustrated in FIG. 1 includes a partial sequence (SEQ ID No: 5) of the antisense strand (bold) of GALNT14 gene. This fragment has two SNPs, i.e., rs9679162 (bold and italicized, indicated by arrow) and rs6752303 (bold and italicized, indicated by arrow). In this example, the first forward primer has the sequence of TCACGAGGCCAACATTCTAG (SEQ ID No: 1), which sequence is complementary to a sequence fragment upstream of the rs9679162; whereas the sequence of the first reverse primer (TTAGATTCTGCATGGCTCAC, SEQ ID No: 2) is identical to a sequence fragment downstream of the rs9679162 (and rs6752303). In the antisense strand, the first SNP rs9679162 has alleles T/G (corresponding bases in the sense strand are A/C), while the second SNP rs6752303 has alleles C/T (i.e., G/A in the antisense strand). Therefore, this primer pair may be used in a PCR-based method to give rise to a 172 base amplicon that includes rs9679162 and rs6752303.

In an optional embodiment, a second pair of primers may be used to facilitate the identification of the SNP genotype of the HCC patients. In particular, the second pair of primers is designed in a way such that the assayed SNP is made as part of a restriction enzyme recognition site, where one genotype at the polymorphic site will constitute as part of the sequence that is recognized by the restriction enzyme, while the other genotype would not. Accordingly, depending on the SNP genotype of the target nucleic acid, amplicons resulted from the use of the second pair of primers may or may not include the restriction enzyme recognizable sequence. Therefore, upon being digested with the restriction enzyme, the amplicons having the assayed SNP will produce polynucleotides that differ in lengths from those that do not contain the assayed SNP.

In one example, the second pair of primers comprises a second forward primer (GAAAGCAAAGAGATATATAT AACGTCT, SEQ ID No: 3) and a second reverse primer (ACCACCTTCCCCTTATTCACCTG, SEQ ID No: 4). In most cases, a primer is completely complementary to the sequence with which the primer hybridized with. However, this is not the case in the present example. As illustrated in FIG. 1, the nucleotides italicized in SEQ ID No:3 (the fourth nucleotide from the 3'-end, G) and No:4 (the fourth nucleotide from the 3'-end, C) are not designed in accordance with conventional rules, rather, they are chosen to introduce restriction enzyme cutting sites of endonuclease BsmAI and BspMI that encompass rs9679162 and rs6752303, respectively (FIG. 1). The allele at the polymorphic site would determine whether the cutting may proceed. In one example, when the genotype of rs9679162 on the antisense strand is G, the amplicon using the antisense strand as a template would have a recognition site GTCTC for BsmAI. In another example, when the genotype of rs6752303 on the sense strand (not shown) is T, the amplicon using the antisense strand as a template would have a recognition site ACCTGC for BspMI. The cutting will result in a fragment (about 55 bases) shorter than the original fragment of 80 bases. The cut and uncut fragments manifest to be the lower and upper bands in the gel image, respectively. This design results in a look up table that genotypes can be called by the band patterns, thereby allowing the assay of these two SNPs.

As discussed hereinabove, the kit may comprise a means for determining the genotype at the polymorphic site.

In one example, the means comprises a restriction endonuclease specific for one of the genotypes at the polymorphic site. For example, in the optional embodiment presented hereinabove, a restriction enzyme recognizing the sequence of GTCTC (such as, BsmAI or isoschizomers thereof) may be used to determine the presence of the genotype of rs9679162 of GALNT14 gene, and a restriction enzyme recognizing the sequence of ACCTGC (such as, BspMI or isoschizomers thereof) may be used to determine the presence of the genotype of rs6752303 of GALNT14 gene.

Alternatively, the determination means may comprise at least one nucleotide probe specific for forming a hybridization complex with a gene fragment comprising one of the genotypes at the polymorphic site. In practice, the probe may be a detectable probe. A detectable probe includes any molecule that specifically binds to a nucleic acid sequence that is being selected for, and which can be labeled so that the required targets can be detected. Examples of detectable label include, but are not limited to, radioactive labels, fluorescent labels, chemiluminescent labels, bioluminescent labels, and enzyme labels.

Still optionally, the kit may comprise an instruction for interpreting the results. The instruction may be included in the kit in either printed or electronic form. Alternatively, the instruction can be provided by way of a link or internet address that provides access to instructions located on either an internet or extranet site. The internet site can be either publicly available or secure.

In particular, the instruction may dictate that the presence of a specified genotype at a specified position predicts complete or partial response of the HCC of the patient. In one embodiment, the specified genotype at the specified position comprises T/T genotype of rs9679162 of GALNT14 gene. Other optional genotypes that are associated with responders are summarized in Table 1.

TABLE 1

Genotype of SNPs associated with responders and non-responders.

| dbSNP ID | Responder Genotype | Non-responder Genotype |
|---|---|---|
| rs1299804 | A/A, A/T | T/T |
| rs10209881 | C/C | C/T, T/T |
| rs6752303 | C/C | T/C, T/T |
| rs9679162 | T/T | G/T, G/G |
| rs5009910 | C/C | T/C, T/T |
| rs12613732 | G/G, G/T | T/T |
| rs7608731 | C/C | C/T, T/T |

The individual components of the kits can be packaged in a variety of containers, e.g., vials, tubes, microtiter well plates, bottles, and the like. Other reagents can be included in separate containers and provided with the kit; e.g., positive control samples, negative control samples, buffers, etc.

Information obtained using the kit described herein is useful for determining if a subject will likely, more likely, or less likely to respond to cancer treatment of a given type. Based on the prognostic information, a doctor can recommend a therapeutic protocol, useful for treating reducing the malignant mass or tumor in the patient or treat cancer in the individual.

In one embodiment, the predicted treatment outcome is the likelihood of survival of an individual having HCC. In another embodiment, the predicted treatment outcome is the likelihood of centric recurrence, including multi-centric recurrence, of the tumor in an individual having HCC. In yet another embodiment, the predicted treatment outcome is the likely timing of centric recurrence, including multi-centric recurrence, of the tumor in an individual having HCC.

Therefore, in another aspect, the present disclosure provides a method for selecting HCC patients suitable for 5-FU-based combination chemotherapy based on the prediction of the responsiveness of HCC patients to a 5-FU-based combination chemotherapy.

According to one embodiment of the present disclosure, the method comprises screening a biological sample derived from the patient for the presence of a T/T genotype of rs9679162 of GALNT14 gene. Our test results indicate that the presence of the T/T genotype is positively related to the tumor suppression effect of the 5-FU-based combination chemotherapy, and therefore, the presence of the T/T genotype in the HCC patient indicates that this HCC patient will respond to the 5-FU-based combination chemotherapy.

Other SNPs that are associated with the responsiveness of the HCC patients to a 5-FU-based combination chemotherapy are summarized in Table 1 above. Therefore, the present method may optionally include the screening for one of more of these SNPs.

The screening step may be performed by using the kit provided hereinabove. However, the present disclosure is not limited thereto, and any conventional method suitable for amplifying and/or genotyping the SNP may be used.

Therefore, in one optional example, the present method may use the first pair of primers having a first forward primer (SEQ ID No:1) and a first reverse primer (SEQ ID No:2). Still optionally, the present method may further use a second pair of primers that comprises a second forward primer (SEQ ID No:3) and a second reverse primer (SEQ ID No:4).

Alternatively, the presence of the desired genotype at the specified position of GALNT14 gene may be determined by various conventional techniques and equivalents thereof. These techniques include, but are not limited to, RFLP analysis, invader assay, single nucleotide primer extension, Taq-Man assay, DASH, molecular beacon assay, direct sequencing, electrophoresis, temperature gradient gel electrophoresis, and SSCP analysis.

In one example, the present method use a restriction enzyme recognizing the sequence of GTCTC (such as, BsmAI or isoschizomers thereof) to determine the genotype of rs9679162. In another example, the present method uses a restriction enzyme recognizing the sequence of ACCTGC (such as, BspMI or isoschizomers thereof) to determine the genotype of rs6752303. In yet another example, the present method may use both the BsmAI and BspMI to determine the genotypes of rs9679162 and rs6752303 at the same time.

In the present disclosure, the 5-FU-based combination chemotherapy means combination chemotherapy that comprises 5-FU and at least one other chemotherapy reagent. In one example, the 5-FU-based combination chemotherapy includes 5-FU, mitoxantrone, and cisplatin; this treatment is also referred to as FMP therapy.

In yet another aspect, the present disclosure is directed to a nucleic acid chip for screening for the GALNT14 gene polymorphism.

According to one embodiment of the present disclosure, the nucleic acid chip comprises a solid support and a first nucleic acid probe immobilized on the solid support. The first nucleic acid probe is specific for detecting the T/T genotype of rs9679162 of GALNT14 gene.

Optionally, the nucleic acid chip comprises one or more additional nucleic acid probes, each of which is specific for detecting SNP genotypes associated with responders, such as those listed in Table 1.

Still optionally, the nucleic acid probe has a detectable label attached thereto. Examples of the detectable label include, but are not limited to, radioactive labels, fluorescent labels, chemiluminescent labels, bioluminescent labels, and enzyme labels.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example I

[Patients Enrollment]

Patients with far advanced HCC were enrolled under the approval of the institutional review board of Chang Gung Memorial Hospital. All of them were treated in Linko Medical Center, Chang Gung Memorial Hospital, Taiwan and gave informed consent. HCC was diagnosed by liver biopsy, aspiration cytology or high α-fetoprotein levels (>400 ng/ml) plus two dynamic image studies (dynamic computer tomography and angiography). All patients with far advanced HCC in the present study had: main portal vein thrombosis and/or extrahepatic metastasis (not suitable for transcatheter arterial chemoembolization); Eastern Cooperative Oncology Group performance status between 0-2; never received systemic chemotherapy except chemoembolization; adequate hematological data (hemoglobin >9 g/dl; white blood cells>2000 cells/mm$^3$; neutrophils>1000 cells/mm$^3$; platelet count>60,000 cells/mm$^3$); adequate liver function (Child-Pugh classification A or B); and adequate renal function (serum creatinine within normal limits). The bilirubin levels were all lesser than 5.0 mg/dl.

A total of 41 subjects with advanced HCC were admitted from January 2007 to November 2009. All patients were followed up until September 2010. The median follow-up time was 29 months.

[Genotyping by Direct Sequencing]

Nuclear DNA was extracted and purified from patients' peripheral blood using QIAamp® DNA blood kit (Qiagen) following the manufacturer's instructions. The quality of isolated genomic DNA was verified using agarose gel electrophoresis and quantities determined using spectrophotometry. A pair of primers, with the sequences 5'-TCACGAGGC-CAACATTCTAG-3'(SEQ ID No: 1) and 5'-TTAGATTCTG-CATGGCTCAC-3' (SEQ ID No:2), were designed for PCR and the direct sequencing of a 172-bp intronic region of GALNT14 gene covering rs9679162, the candidate predictor of FMP response. Conventional Sanger sequencing was performed using the Applied Biosystems 3700 instrument.

[Treatment Protocols]

The treatment was conducted after the genotyping, but all patients were treated with the same protocol described herein. 5-fluorouracil was administered continuously via an intravenous route at a dose of 450 mg/m$^2$ from days 1-5. Mitoxantrone was administered as an intravenous infusion at a dose of 6 mg/m$^2$ on day 1. Cisplatin was administered as an intravenous infusion at a dose of 80 mg/m$^2$ over 2 h on day 1 with standard hydration. The does used in the subsequent course was adjusted according to the toxicities observed. Granulocyte colony-stimulating factor was administered when neutropenia and/or leukocytopenia of grade 3/4 was observed. The treatment was repeated every 4-6 weeks until maximum of six courses was reached or until patients were unsuitable for further chemotherapy.

[Assessment of Tumor Response]

The objective tumor response was assessed by computer tomography every 4-8 weeks after the beginning of FMP therapy and was evaluated according to the following Response Evaluation Criteria In Solid Tumors criteria. Complete response was defined as the complete disappearance of all target lesions without any residual lesion. Partial response was defined as a >30% decrease in tumor mass, without progression in any target lesion or appearance of a new lesion. Stable disease was defined as either a <30% decrease or a <20% increase of total tumor mass. Progressive disease was defined as a >20% increase in total tumor mass or appearance of a new lesion. Disease control was achieved in patients without progressive disease. Adverse effects were evaluated according to the NCI Common Terminology Criteria for Adverse Events version 3.0.

[Statistical Analysis and Data Processing]

Survival analysis was performed based on stratification of patients according to their genotypes. We stratified patients into two groups based on the dominant/recessive mode of inheritance. The corresponding two survival curves (Kaplan-Meier method) were then compared by the log-rank test and the Wilcoxon test using the PAST statistical software.

[Results]

Demographic, baseline and treatment characteristic of patients enrolled in the study were summarized in Table 2.

TABLE 2

Demographic, baseline, and treatment characteristics of patients enrolled.

|  | Patients with disease progression | Patients achieving disease control | P |
|---|---|---|---|
| Number of patients | 28 | 13 |  |
| Sex (male) | 24 (85.7%) | 9 (69.2%) | NS |
| Age (years) | 55.0 ± 17.1 | 57.6 ± 9.5 | NS |
| Anti-HCV (positive) | 7 (25.0%) | 6 (46.2%) | NS |
| HBsAg (positive) | 21 (75.0%) | 7 (53.8%) | NS |
| ECOG performance status |  |  |  |
| 0 | 11 (39.3%) | 8 (61.5%) | NS |
| 1 | 8 | 5 |  |
| 2 | 9 | 0 |  |
| Diagnosis |  |  |  |
| Image + alpha-fetoprotein | 16 (57.1%) | 4 (30.8%) | NS |
| Cytology | 6 | 3 |  |
| Histology | 6 | 6 |  |
| Okuda stage |  |  |  |
| 1 | 8 (28.6%) | 7 (53.8%) | NS |
| 2 | 16 | 4 |  |
| 3 | 4 | 2 |  |
| Cirrhosis | 26 (92.9%) | 13 (100%) | NS |
| Main portal vein thrombosis (yes) | 15 (53.6%) | 8 (61.5%) | NS |
| Extrahepatic metastasis (yes) | 14 (50.0%) | 8 (61.5%) | NS |
| Largest tumor diameter (cm) | 8.9 ± 4.3 | 6.2 ± 4.9 | NS |
| Child-Pugh classification |  |  |  |
| A | 15 (53.6%) | 8 (61.5%) | NS |
| B | 13 | 5 |  |
| Alpha-fetoprotein (ng/mL) | 48880.1 ± 84385.2 | 5401.8 ± 12037.3 | NS |
| Creatinine (mg/dL) | 0.8 ± 0.3 | 0.9 ± 0.3 | NS |

TABLE 2-continued

Demographic, baseline, and treatment characteristics of patients enrolled.

|  | Patients with disease progression | Patients achieving disease control | P |
|---|---|---|---|
| AST (U/L) | 105.0 ± 90.2 | 80.7 ± 69.0 | NS |
| White blood cells (×1000) | 7.2 ± 3.4 | 6.2 ± 2.4 | NS |
| Neutrophil (×1000) | 5.3 ± 3.1 | 3.9 ± 1.6 | NS |
| Hemoglobin (g/dL) | 12.0 ± 2.1 | 11.9 ± 1.4 | NS |
| Platelet (×1000) | 207.0 ± 110.7 | 174.8 ± 89.7 | NS |
| Alcoholism (yes) | 14 (50.0%) | 7 (53.8%) | NS |
| Previous treatment (yes)* | 17 (60.7%) | 3 (23.1%) | 0.043 |
| Courses of FMP received |  |  |  |
| 1 | 22 (78.6%) | 3 (23.1%) | 0.001 |
| ≥2 | 6 | 10 |  |
| Median time-to-progression (months) | 2.0 (2.1-4.1) | 6.8 (2.0-22.0) | <0.001 |
| Median overall survival (months) | 3.8 (2.0-13.1) | 9.5 (3.5-23.7) | 0.010 |
| Grade 3/4 adverse events |  |  |  |
| Leukopenia | 6 (21.4%) | 1 (7.7%) | NS |
| Neutropenia | 5 (17.9%) | 0 | NS |
| Thrombocytopenia | 2 (7.1%) | 1 (7.7%) | NS |
| Fatigue | 1 (3.6%) | 0 | NS |
| Anemia | 2 (7.1%) | 0 | NS |
| Bleeding | 0 | 1 (7.7%) | NS |
| Infection | 2 (7.1%) | 1 (7.7%) | NS |
| Mucositis | 2 (7.1%) | 0 | NS |
| Diarrhea | 0 | 2 (15.4%) | NS |
| TT homologous genotype for rs9679162 | 8 (28.6%) | 10 (76.9%) | 0.0063 |

*In 17 patients with disease progression, 12 received only TACE, 3 received operation followed by TACE, 2 received radiotherapy. In 3 patients with disease control, all received only TACE.

In the total of 41 patients, 13 subjects (responders) achieved disease control while the cancerous disease in the remaining 28 subjects (non-responders) progressed. The response rate was 31.7% (Table 2). No significant difference in age, sex and various baseline characteristics were found between the two groups (Table 2).

Overall survival was calculated from the date of treatment to the date of death or last follow-up. Progression-free survival was calculated from the date of treatment to the date of progressive disease. Except for two patients who were still alive at the end of the study, all other patients were followed until death. All of the survival data were updated to September 2010 when the data analysis on the therapeutic responses and survivals were conducted.

The two groups (non-responders versus responders) manifested significant difference in the median progression-free survivals (2 and 6.8 months, respectively) and overall survivals (3.8 and 9.5 months, respectively). The biochemistry and hemogram data presented in Table 2 were baseline values.

The relationship between the genotype of rs9679162 and the objective response to the first FMP course is summarized in Table 3.

TABLE 3

Relationship between the genotype of rs9679162 and the objective response to the first FMP course.

| Patients with disease progression | | Patients with disease control | | $\chi^2$ p | Fisher's exact p |
|---|---|---|---|---|---|
| TT | GG & GT | TT | GG & GT | (2 tailed) | (2 tailed) |
| 8 | 20 | 10 | 3 | 0.003695 | 0.006326 |

In both one degree-of-freedom $X^2$ test and the Fisher's exact test, small probability (p) values were observed, which indicated that the genotype is associated with the objective response to FMP treatment.

Since responders were encouraged by the positive initial outcome to receive more cycles of FMP treatment, the two groups received different average numbers of FMP courses (Table 2). As a result, the survival curves of overall and progression-free survival were confounded by FMP courses. However, the number of FMP courses is a consequence of initial responses which are associated with genotypes. It would thus be interesting to follow the survivals based on genotype.

Figure 2:
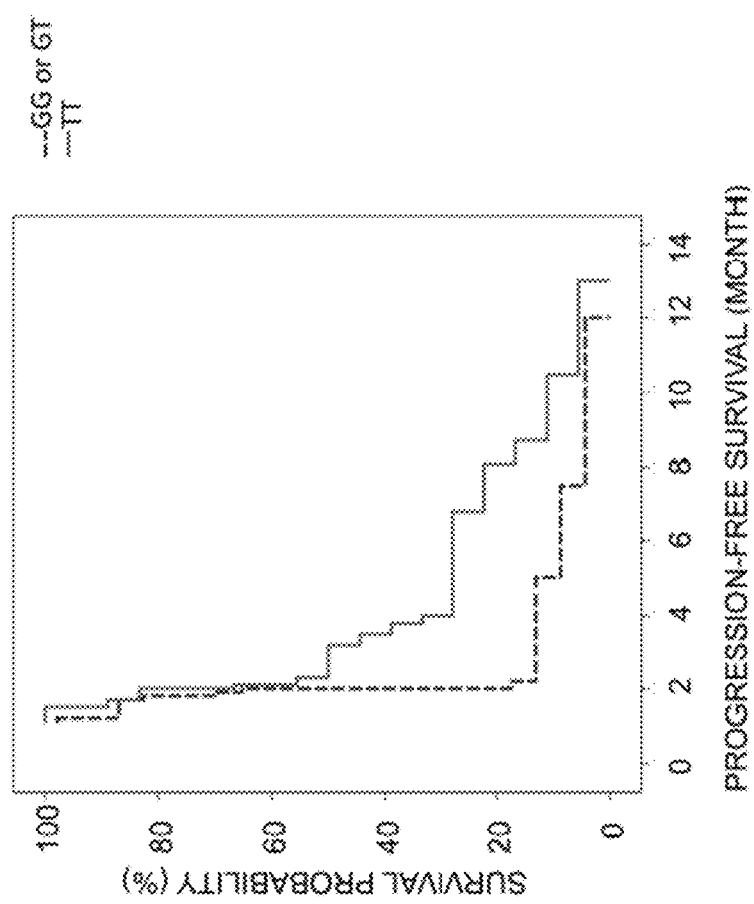
FIG. 2 is a graph illustrating the Kaplan-Meier survival curve of patients stratified by their rs9679162 genotypes.

In this analysis, patients were stratified into two groups, the 'TT' group and the 'GG+GT' group, according to their genotypes on rs9679162. The Kaplan-Meier curves of progression-free of the two groups are shown in FIG. 2. In the 41 patients (dominant G allele: n=23; recessive T allele: n=18), difference was observed in the progression-free survival (p=0.01485).

Example II

In this example, the performance of the SNP assay proposed in the present disclosure was evaluated.

A restriction enzyme cutting site is usually 5-6 nucleotides in length. It is uncommon that a natural restriction site sequence pattern appears in the proximity of the assayed SNP. Thus we employed the genetic engineering method to introduce a restriction enzyme cutting site artificially. The assay was based on nested-PCR method. A first PCR was performed to obtain the DNA amplicons containing the SNP of interest. The second PCR employ a set of specially designed primers to convert an allele form of the SNP into a restriction enzyme cutting site. Sequences were sufficiently amplified then treated by the corresponding restriction enzyme.

To evaluate the performance of the assay, clinical samples from 245 HCC patients were obtained from tissue bank of Chang Gung Memorial Hospital with informed consents. Samples were obtained from liver surgery, and the non-tumor parts were selected. DNA molecules were extracted from these samples. The DNA molecules were amplified using a first forward primer (SEQ ID No:1) and a first reverse primer (SEQ ID No:2). Then, a second forward primer (SEQ ID No:3) and a second reverse primer (SEQ ID No:4) were used to introduce the cutting sites of BsmAI and BspMI which cover rs9679162 and rs6752303 respectively (FIG. 1). PCR products were then digested with both BsmAI and BspMI. FIG. 3 gives an exemplified gel image of the proposed assay of 5 subjects. Both homozygous and heterozygous genotypes can be successfully obtained by the method of this invention.

Sanger sequencing was also performed to the amplicon to serve as the benchmark of performance. The concordance of results using the proposed assay and the Sanger sequencing is 100%.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for identifying single nucleotide polymorphisms (SNP) of a target nucleic acid in a patient suffering from hepatocellular carcinoma for selecting a therapy for the patient, comprising, obtaining a nucleic acid-containing sample from the patient;

detecting the presence of at least one SNP genotype in the target nucleic acid of the nucleic acid sample using a polymerase chain reaction (PCR) based method, wherein the at least one SNP genotype comprises a T/T genotype of rs9679162, and the PCR-based method comprises, using a first forward primer having the sequence of SEQ ID No: 1 and a first reverse primer having the sequence of SEQ ID No: 2 to amplify the nucleic acid-sample to give rise to a first amplicon, using a second forward primer having the sequence of SEQ ID No: 3 and a second reverse primer to amplify the first amplicon to give rise to a second amplicon, reacting the second amplicon with a first restriction enzyme that recognizes the sequence of GTCTC in the target nucleic acid to perform a first restriction digestion reaction to give rise to a first digestion product, and determining the presence of the T/T genotype of rs9679162 when the first digestion product consists essentially of non-digested fragment; and selecting a 5-fluorouracil (5-FU) based combination chemotherapy for the patient when the detection result indicates the presence of the at least one SNP genotype.

2. The method of claim 1, wherein the 5-FU-based combination chemotherapy consists of 5-FU, mitoxantrone, and cisplatin.

3. The method of claim 1, wherein the second reverse primer has the sequence of SEQ ID No: 4.

4. The method of claim 1, wherein the at least one SNP genotype further comprises A/A and A/T genotype of rs1299804, C/C genotype of rs10209881, C/C genotype of rs6752303, C/C genotype of rs5009910, G/G and G/T genotype of rs12613732, and C/C genotype of rs7608731.

5. The method of claim 1, wherein the at least one SNP genotype further comprises C/C genotype of rs6752303, the second reverse primer has the sequence of SEQ ID No: 4, and the PCR-based method further comprises, using the second amplicon to react with a second restriction enzyme that recognizes the sequence of ACCTGC in the target nucleic acid to perform a second restriction digestion reaction to give rise to a second digestion product; and determining the presence of the C/C genotype of rs6752303 when the second digestion product consists essentially of at least one digested fragment.

6. The method of claim 5, wherein the first and second restriction digestion reactions are performed in a single reaction.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tcacgaggcc aacattctag                                                    20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ttagattctg catggctcac                                                    20

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
gaaagcaaag agatatatat aacgtct                                            27

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
accaccttcc ccttattcac ctg                                                23

<210> SEQ ID NO 5
<211> LENGTH: 172
<212> TYPE: DNA
<213> ORGANISM: Artificial Sequence
<220> FEATURE:
<223> OTHER INFORMATION: amplicon
```

```
<400> SEQUENCE: 5
agtgctccgg ttgtaagatc gttctcctct gtctttcgtt tctctatata tattggagag        60
accaccactg tttacgatac ttcttttttg tcgacttatt ccccttccac caggtctgtt       120
cagaaccttc tccactccaa gtcatcctcc ctcactcggt acgtcttaga tt              172
```